US009155306B2

(12) United States Patent
Radabaugh et al.

(10) Patent No.: US 9,155,306 B2
(45) Date of Patent: Oct. 13, 2015

(54) METHODS FOR THE PRODUCTION OF GRANULAR COMPOSITE PESTICIDAL COMPOSITIONS AND THE COMPOSITIONS PRODUCED THEREBY

(75) Inventors: Robert M. A. Radabaugh, Marysville, OH (US); Jonathan C. Raistlin Newton, Columbus, OH (US)

(73) Assignee: OMS Investments, Inc., Los Angeles, CA (US)

( * ) Notice: Subject to any disclaimer, the term of this patent is extended or adjusted under 35 U.S.C. 154(b) by 1028 days.

(21) Appl. No.: 11/977,233

(22) Filed: Oct. 24, 2007

(65) Prior Publication Data

US 2008/0103048 A1    May 1, 2008

Related U.S. Application Data

(60) Provisional application No. 60/854,573, filed on Oct. 26, 2006.

(51) Int. Cl.
| A01N 53/00 | (2006.01) |
| A01N 43/70 | (2006.01) |
| A01N 25/10 | (2006.01) |
| A01N 25/22 | (2006.01) |
| A01N 25/26 | (2006.01) |

(52) U.S. Cl.
CPC .............. *A01N 43/70* (2013.01); *A01N 53/00* (2013.01)

(58) Field of Classification Search
CPC .............................. A01N 43/70; A01N 53/00
USPC ....................................................... 504/367
See application file for complete search history.

(56) References Cited

U.S. PATENT DOCUMENTS

| 4,028,464 A | 6/1977 | Bell et al. |
| 4,198,397 A | 4/1980 | Gillings et al. |
| 4,216,283 A | 8/1980 | Cooper et al. |
| 4,238,505 A | 12/1980 | Engel |
| 4,268,553 A | 5/1981 | Marzouki et al. |
| 4,291,052 A | 9/1981 | Gillings et al. |
| 4,367,276 A | 1/1983 | Cooper et al. |
| 4,368,250 A | 1/1983 | Cooper et al. |
| 4,370,400 A | 1/1983 | Cooper et al. |
| 4,411,093 A | 10/1983 | Stout et al. |
| 5,022,917 A | 6/1991 | Allan |
| 5,371,105 A | 12/1994 | Damo et al. |
| 5,849,320 A * | 12/1998 | Turnblad et al. ............... 424/410 |
| 6,036,971 A | 3/2000 | Kimoto et al. |
| 6,084,010 A | 7/2000 | Baetzold et al. |
| 6,251,415 B1 | 6/2001 | Herbert |
| 6,254,655 B1 | 7/2001 | Goertz |
| RE37,683 E | 4/2002 | Briddell et al. |
| 6,403,308 B1 | 6/2002 | Prichard et al. |
| 6,460,290 B1 | 10/2002 | Moore et al. |
| 6,514,951 B1 | 2/2003 | Wood et al. |
| 6,593,087 B2 | 7/2003 | Prichard et al. |
| 6,826,866 B2 | 12/2004 | Moore et al. |
| 6,884,756 B2 | 4/2005 | Lynch et al. |
| 7,015,177 B2 | 3/2006 | Knott et al. |
| 2002/0115565 A1 * | 8/2002 | Asrar et al. ................... 504/100 |
| 2003/0190666 A1 | 10/2003 | Prichard et al. |
| 2004/0116560 A1 | 6/2004 | Panek et al. |
| 2005/0054537 A1 | 3/2005 | Muller et al. |
| 2006/0034900 A1 | 2/2006 | Saeki et al. |
| 2007/0072775 A1 * | 3/2007 | van Boxtel-Verhoeven et al. ............................. 504/367 |
| 2007/0104749 A1 * | 5/2007 | Birthisel et al. ............... 424/405 |

OTHER PUBLICATIONS

Atrazine. Fact Sheet [online]. Compendium of Pesticide Common Names [retrieved on May 22, 2009]. Retrieved from the Internet: <URL: http://www.alanwood.net/pesticides/index_cn_frame.html.*
Scotts Product Guide: Scotts® Bonus® S Weed and Feed, (http://www.scotts.com/index.cfm/event/ProductGuide.product/documentld/80ee31ad932 . . . ).
Scotts Product Guide, (http://www.scotts.com/index.cfm/event/ProductGuide.product/documentld/0efbb24d1d6c7 . . . ).
Notification of Transmittal of the International Search Report and the Written Opinion of the International Searching Authority, or the Declaration, dated Mar. 13, 2008.

* cited by examiner

*Primary Examiner* — Sue Liu
*Assistant Examiner* — Andriae M Holt
(74) *Attorney, Agent, or Firm* — Hunton & Williams LLP

(57) ABSTRACT

Methods are provided for the production of granular composite compositions including at least two pesticidally active ingredients in combination such as insecticidally active and herbicidally active ingredients and to the composite combination products produced thereby.

31 Claims, No Drawings

METHODS FOR THE PRODUCTION OF GRANULAR COMPOSITE PESTICIDAL COMPOSITIONS AND THE COMPOSITIONS PRODUCED THEREBY

CROSS-REFERENCE TO RELATED APPLICATION

This application claims priority to Provisional Application 60/854,573, filed Oct. 26, 2006, which is incorporated herein in its entirety.

BACKGROUND OF THE INVENTION

1. Field of the Invention

This invention relates to methods for the production of composite pesticidal compositions and to the compositions produced thereby. More particularly, it relates to methods for producing granular composite compositions including at least two pesticidally active ingredients in combination such as an insecticidally active ingredient and a herbicidally active ingredient and to the composite combination products produced.

2. Description of Related Art

A wide variety of pesticidal compositions for use in treating plants have been known heretofore which include insecticidally active ingredients and/or herbicidally active ingredients. Additionally, a variety of methods for producing such pesticidal compositions are known and, particularly, methods for producing products including separate, individual ones of the pesticidal agents. For example, The Scotts Company LLC has previously offered a commercially available product under the trademark "Bonus" S for use as a broad leaf weed killer, particularly, in St. Augustinegrass, centipede, zoysia and carpetgrass lawns. This product consists of a herbicidally active Atrazine powder tacked onto a granular urea-formaldehyde fertilizer core material employing polybutene L-14 as the tacking agent.

Another currently available commercial product being offered by The Scotts Company LLC under the tradename "Turf Builder with Fire Ant Killer" is used primarily for fire ant control and consists of an insecticidally active solution of a pyrethroid ingredient (Bifenthrin) which is sprayed onto a granular urea-formaldehyde fertilizer.

However, there has been a continuing unfulfilled need to provide efficient and cost effective methods for producing granular composite compositions comprising combinations of certain pesticidally active ingredients such as mixtures of insecticidally active ingredients and herbicidally active ingredients as well as the unique compositions produced by such methods.

For example, it has been recognized heretofore that it would be of significant economic and functional benefit to provide improved methods for producing composite granular compositions that would solve several troubling problems which consumers have encountered in regard to lawn care in hot, dry climates such as found in the southern United States. In particular, it would be highly advantageous to provide methods for producing a unitary composite composition that is capable of killing and/or preventing fire ants in such lawns and would be effective for eradicating weeds from the lawns while providing enhancements in feeding and strengthening the lawns whereby preventing browning and bare spots in the grass under prevailing heat and drought conditions.

Also, it would be advantageous to provide such unitary, granular composite compositions which exhibit these desirable functional characteristics.

As noted above, a wide variety of pyrethroid compositions have been known to be effective active ingredients for inclusion in insecticidal formulations for controlling fire ants. However, problems have been encountered in attempting to formulate composite products containing pyrethroid compositions in combination with other pesticidally active ingredients. That is, the pyrethroid compositions have been known to exhibit solubility problems which render them commercially unacceptable for formulation as sprays to enable efficient and cost effective application on granular active ingredient substrates such as powdered herbicidally active ingredients or on granular inert carriers.

Specifically, it has been known that pyrethroid compounds such as alphamethrin, cyfluthrin cypermethrin (alpha, beta, theta, zeta), deltamethrin, fenpropathrin, fenvalerate, flucythrinate, fluvalinate and tralomethrin which are all cyano-containing compounds are only soluble in highly polar solvents.

However, it has been recognized that the use of such highly polar solvents to dissolve these pyrethroids results in solutions which lack the necessary tackiness to effectively adhere granular active ingredients to substrates when sprayed thereon. Furthermore, to the extent that solutions of these cyano containing pyrethroid insecticidally active ingredients are dissolved in the necessary highly polar solvents to produce sprays and are capable of being applied on granular active ingredient substrates such as herbicidally active ingredients, it has been found that the presence of the highly polar solvents in addition to reducing tackiness of the spray, also causes deterioration of the effectiveness of the composite active ingredients in the compositions including the insecticidally active pyrethroid and any other insecticidally or herbicidally active composition in the composite product.

However, no previously known methods have been available which are suitable for producing unitary, granular composite pesticidal compositions having the desired characteristics either because of process or product shortcomings such as the cost effectiveness of the methods, the ability to include the desired active ingredients efficiently and effectively in the composite compositions and the physical properties of the resulting compositions produced thereby.

SUMMARY OF THE INVENTION

Accordingly, it is a primary object of the present invention to provide efficient and cost effective methods for producing unitary composite granular compositions containing at least two pesticidally active ingredients therein such as at least one insecticidally active ingredient with at least one other active ingredient, preferably a herbicidally active ingredient.

It is a further object of the present invention to provide unitary composite granular compositions containing at least two pesticidally active ingredients therein such as at least one insecticidally active ingredient with at least one other active ingredient, preferably a herbicidally active ingredient.

Other objects are to provide unitary granular composite compositions and methods for producing such composite compositions which exhibit desired physical and chemical properties, for example, in regard to the treatment of lawns to kill and/or prevent fire ants therein while effectively eradicating weeds from the lawns and, also, providing enhanced feeding and strengthening of the lawns, for example, by preventing browning and/or bare spots in the lawn under heat and drought conditions as encountered in treatment of lawns in the southern United States.

A further object is to provide methods for producing granular compositions wherein certain pesticidally active ingredients such as insecticidally active ingredients are dissolved in suitable solvents to produce sprayable solutions for application on granular substrates in a manner such that unitary composite granular products are formed containing the pesticidally active ingredients in combination with other active ingredients such as insecticidally and/or herbicidally active ingredients that are adhered or tacked to the pesticidally active ingredients.

A more specific object is to provide methods for producing granular composite compositions containing at least one insecticidally and at least one herbicidally active ingredient in a unitary granular product by spraying a tackifying solution containing the insecticidally active ingredient, such as bifenthrin, on an outer surface of granular substrate such as a standard fertilizer granule or an inert carrier and adhering a granular composition such as a small grain or powdered pesticidally active ingredient, most preferably, a herbicidally active ingredient such as atrazine powder to the sprayed outer surface of the substrate.

Another general object is to provide compositions containing at least one pesticidally active ingredient such as an insecticidally active ingredient and at least one other pesticidally active ingredient such as a herbicidally active ingredient in a unitary, granular, composite formulation.

A still further object is to provide composite products containing at least one insecticidally active pyrethroid ingredient and at least one other active ingredient such as at least one herbicidally active ingredient, preferably, atrazine, in a unitary granular formulation for use in treating lawns to kill and/or prevent fire ants while effectively eradicating weeds from the lawns and, also, providing enhanced feeding and strengthening of the lawns, for example, by preventing browning and/or bare spots in the lawn under heat and drought conditions.

The foregoing and other objects of this invention are achieved by providing methods comprising dissolving at least one pesticidally active ingredient in a suitable solvent to form a tackifying solution and coating the tackifying solution on a substrate material and then adhering at least one small grain or powdered granular pesticidally active ingredient to the pesticidally active ingredient coating on the substrate to form a unitary, composite composition containing both the dissolved pesticidally active ingredient and the small grain or powdered granular pesticidally active ingredient.

DETAILED DESCRIPTION

In a preferred embodiment, the methods of the present invention comprise dissolving at least one pesticidally active ingredient such as an insecticidally active ingredient in a suitable solvent and spraying the resulting tackifying solution on the outer surface of a desired granular substrate and applying a granular pesticidally active ingredient such as a herbicidally active ingredient, preferably in small grain or powdered form, on the spray coated outer surface of the granular substrate to adhere the granular active ingredient to the outer surface of the spray coated granular substrate to bind the pesticidally active ingredients into a unitary composite granular product. As employed herein, the terms “small grain” and/or “powdered” material refers to particulate and/or granular materials or products which are sized to pass through a 60 mesh US standard screen and have a size of less than about 250 μm.

In a particularly preferred embodiment, the methods of the present invention comprise dissolving at least one non-cyano containing pyrethroid insecticidally active ingredient to form a coating solution.

A compound which exemplifies a particularly preferred non-cyano containing pyrethroid for use herein is bifenthrin which is known to be effective against a broad range of pests and is described in U.S. Pat. No. 4,238,505 and has the following structure:

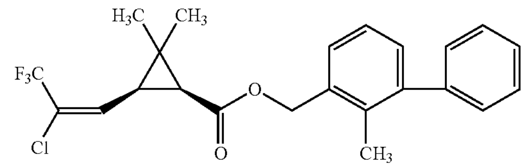 [SMILES: Cc1c(COC(=O)[C@H]2[C@@H](/C=C(/Cl)C(F)(F)F)C2(C)C)cccc1-c1ccccc1]

Examples of other non-cyano containing pyrethroid compositions which are suitable for use herein are allethrin, barthrin, bioallethrin, bioresmethrin, biopermethrin, dimethrin, esbiol, furethrin, permethrin, resmethrin, tetramethrin and, particularly, bifenthrin, and mixtures thereof.

In accordance with the present invention, the non-cyano containing pyrethroid compositions are dissolved in a suitable non-polar solvent such as a polybutene having the following structure to form a tackifying solution:

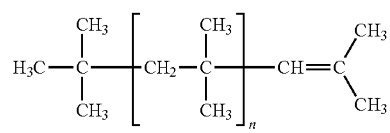

wherein n is in a range of about 2 to 20, preferably about 4 to 6.

Other non-polar solvents which may be employed to dissolve the insecticidally active ingredients and to form a tackifying type solution for use herein include such naturally occurring materials as cottonseed oil, linseed oil, soybean oil, canola oil, coconut oil, corn oil, fish oil, hydrogenated vegetable oils, fatty acid esters such as isopropyl myristate, olive oil, palm oil, paraffin wax, peanut oil, safflower oil and mineral oil. Other non-polar solvents which may be employed herein include greater than 10 carbon alkenes, polymerized alpha ollefins, oxidized plant oils such as castor oil, linseed oil polymerizates, methyl oleate, pine oil, petrolatum, PPG mono oleate and rape oil methyl ester.

In a preferred embodiment of this invention, bifenthrin is employed as the insecticidally active ingredient in the compositions and the non-polar solvent employed to dissolve the insecticidally active ingredient is a polybutene such as L-14 sold by Amoco Corporation under the trade name Indopol. Polybutene L-14 has previously been considered to be a poor solvent but in the methods of the present invention, it was found that bifenthrin and, in particular, bifenthrin technical is soluble and stable in polybutene L-14 over a range of concentrations and that polybutene L-14 presents no problems in regard to tacking or adhering a small grain or powdered pesticidally active ingredient such as atrazine to a substrate sprayed with the bifenthrin/polybutene L-14 tackifying solution. Also, other polybutenes such as those designated as L-50, H-7 and H-8, respectively, have been found to be particularly suitable for use as a solvent herein. These polybutene compositions have the following structure:

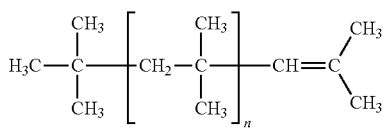

wherein n=4.59 for polybutene L-14 which has a molecular weight of about 370; n=5.66 for polybutene L-50 which has a molecular weight of about 430; n=5.84 for polybutene H-7 which has a molecular weight of about 440 and n=6.73 for polybutene H-8 which has a molecular weight of about 490.

In particular, it has been found that the use of the polybutene L-14, polybutene L-50, polybutene H-7 and/or polybutene H-8 in the tackifying solutions employed in the present invention advantageously prevents degradation of the substrate such as a fertilizer bases and, also, prevents pesticide interaction of the combination pesticidally active ingredients. Another advantage is that since the components of the composite product can be introduced individually, the rates of the pesticidally active ingredient such as bifenthrin in the compositions of this invention as well as the volume of polybutene to be used in forming the tackifying solution can be readily adjusted to optimize the amount of tackiness the formulations for adhering the granular pesticide such as technical atrazine powder.

The solution containing at least one non-cyano containing pyrethroid insecticidally active ingredient dissolved in the non-polar solvent has a tacky consistency so that in accordance with the methods of the present invention, the solution may be sprayed on the outer surface of a desired granular substrate such as a fertilizer granule or an inert carrier or the like or may be spray applied directly with at least one granular pesticidally active ingredient to form a unitary granular composite composition.

However, in a most preferred embodiment, the tackifying solution containing the dissolved pesticidally active agent is sprayed on the outer surface of a granular substrate and then a further granular pesticidally active ingredient such as a herbicidally active ingredient, preferably in powdered form, is applied on the spray coated outer surface of the granular substrate and the further granular active agent is adhered to the outer surface of the spray coated granular substrate as a result of the tackifying action of the coating solution to bind the pesticidally active ingredients, preferably, the insecticidally active ingredient and the herbicidally active ingredient into a unitary composite granular product.

A wide variety of small grain or powdered pesticidally active agents may be employed for use as the granular active agents to be adhered to the outer surface of the spray coated granular substrate. Examples of some of such granular active agents are pesticides including herbicides, insecticides fungicides and the like.

Suitable herbicides for use as granular active ingredients herein include such materials as 2,4-D, 2,4-DP-p, Ametryn, Amicarbazone, Atrazine, Benefin, Bensulide, Bentazone, Bromoxynil, Butralin, Calar (Calcium Acid methanearsenate), Carfentrazone, Chlorflurenol-methyl, Chlorthal-dimethyl, Clopyralid, Dicamba, Diflufenzopyr, Diquat, Dithiopyr, DMA Salt of Dicamba, DMA Salt of 2,4-D, DMA Salt of MCPA, DMA Salt of MCPP, DMA Salt of MCPP-p, Fluazifop-P-butyl, Fluroxypyr-methyl, Glufosinate, Glyphosate, Halosulfuron-methyl, Imazapyr, Imazaquin, Isoxaben/Gallery, MCPP, MCPA, MCPP-p, Mesotrione, Metolachlor, s-Metolachlor, Metsulfuron Methyl, Oryzalin, Oxadiazon, Oxyfluorfen, Pendimethalin, Penoxsulam, Prodiamine, Prometon, Quinclorac, Siduron, Thiazopyr, Topramazone, Triclopyr, Trifluralin, Vemolate and the like and mixtures thereof.

Suitable insecticides for use as granular active ingredients herein include such materials as Acephate Bacillus Thuringiensis, Bendiocarb, Bifenazate, Bromophos, Bifenthrin, Carbaryl, Chlorpyrifos, Clothianadin, Cypermethrin, Deltamethrin, Diazinon, Ethion, Ethofumesate, Esfenvalerate, Fenoxycarb, Floramite/Bifenazate, Halofenozide, Imidacloprid, Indoxacarb, Isofenphos, Malathion, Permethrin, d-Phenothrin, Propetamphos, Propoxur, Pyrethrin, Pyriproxifen, Resmethrin, Rotenone, Spinosad, Tebufenozide, Tetramethrin, Thiamethoxam, Trichlorfon, Zeta-cypermethrin and the like and mixtures thereof.

Suitable fungicides for use as granular active ingredients herein include such materials as Aliette (Fosetyl-aluminum), Anilazine, Atrazine, Azoxystrobin, Benomyl, Binapacryl, Captafol, Captan, Chloroneb, Chlorothalonil, Cyfluthrin, Etridiazole, Fluoxastrobin, Flutolanil, Iprodione, Mancozeb, Metalaxyl, Metaldehyde, Metolachlor, Myclobutanil, PCNB, Propiconazole, Thiophanate-methyl, Thiram, Triademefon, Triforine, Vinclozolin, Zineb, Ziram and the like and mixtures thereof.

With regard to substrates on which the pesticidally active ingredients may be applied as by spraying or drum coating in accordance with the present invention, suitable materials include a wide variety of granular materials including standard agriculturally acceptable inert carrier materials; standard fertilizer granules such as uncoated fertilizers; coated fertilizer granules and the like.

Exemplary of suitable inert carriers for use herein include such materials as corn cobs, peanut hulls, coffee been husks, pelletized limestone and dolomite, biological granules and the like and mixtures thereof.

Suitable fertilizer granules for use as substrates herein include standard NPK type fertilizers which may include methylene urea nitrogen sources, phosphorus sources, single superphosphates, triple superphosphates, calcium phosphates, nitro phosphates, potassium phosphates, ammonium phosphates, ammoniated superphosphates and the like and mixtures thereof. Further fertilizer granules suitable for use in the methods of this invention include potassium sources such as muriate of potash, potassium sulfates, potassium phosphates, potassium hydroxides, potassium nitrates, potassium carbonates and bicarbonates, potassium magnesium sulfates and the like and mixtures thereof.

Additional fertilizer granules suitable for use in the methods of this invention include secondary nutrient sources such as elemental sulfur, calcium and magnesium salts including phosphates, oxides, sulfates, carbonates, chlorides, nitrates and the like and mixtures thereof. Still further fertilizer granules suitable for use in the methods of this invention include micronutrient sources such as iron, manganese, copper, boron, zinc and molybdenum salts such as phosphates, oxides, sulfates, carbonates, chlorides, nitrates, borates, molybdates and the like and mixtures thereof as well as chelates of micro nutrients such as EDTA chelates and the like.

Representative materials that may be used as dry micronutrient substrates in the methods of the present invention specifically include calcium nitrate, magnesium sulfate, magnesium nitrate, ferrous sulfate, ferrous nitrate, manganese sulfate, manganese nitrate, copper sulfate, copper nitrate, boric acid, sodium borate, zinc sulfate, zinc nitrate, sodium molybdate, ammonium molybdate and the like.

In regard to coated fertilizer granules for use as substrates for forming the compositions of the present invention, one type of coated fertilizer granule preferred for use herein as a substrate is a controlled release fertilizer (CRF) granule such as a sulfur-coated fertilizer as exemplified by the fertilizers described in U.S. Pat. Nos. 3,295,950; 3,342,577; 3,576,613; 3,903,333; 4,042,366; 4,636,242; 4,857,098; 4,881,963; 5,219,465; 5,405,426; 5,599,374 and 6,338,746.

Another type of CRF granule preferred for use is a polymer coated granule including a solvent applied polymer coating. The polymeric material applied to these granules may be either a thermosetting resin or a thermoplastic. Examples of solvent applied thermosetting resin coated fertilizers which are suitable for use herein are disclosed in U.S. Pat. Nos. 3,223,518; 4,657,576 and 4,880,455, whereas examples based on thermoplastics can be found in U.S. Pat. No. 4,019,890. Of particular note are the granular CRF products described in U.S. Pat. No. 6,039,781.

Other polymer coated fertilizers for use as substrates herein are described in U.S. Pat. Nos. 5,374,292; 5,547,486; 5,652,196; 5,858,094; 5,993,505; 6,139,597; 6,254,655; 6,312,493; 6,656,882; 6,787,234 and 6,987,082. Another exemplary polymer encapsulated fertilizer which may be used as a substrate herein is a latex coated granular fertilizer such as the fertilizers disclosed in U.S. Pat. Nos. 4,549,897 and 5,186,732.

Accordingly, in a preferred embodiment of the methods of this invention, a tackifying spray solution is formed by dissolving at least one non-cyano containing pyrethroid insecticidally active ingredient in a non-polar solvent and spraying the resulting tackifying solution on a granular substrate to spray coat the tackifying solution on an outer surface of the granular substrate. Then, a small grain or powdered granular pesticidally active ingredient such as a powdered herbicidally active ingredient is applied on the spray coated outer surface of the granular substrate so that the tackifying solution sprayed on the outer surface of the granular substrate causes the powdered herbicidally active ingredient to adhere to the outer surface of the spray coated granular substrate binding the insecticidally active ingredient with the herbicidally active ingredient.

By producing the compositions in accordance with the methods of the present invention, it has been found that the tackifying coating promotes enhanced physical stability of the resulting granular composition and provides a shielding effect preventing degradation of the pesticidally active ingredients in the granular compositions.

The compositions produced by the methods of the present invention have been found to exhibit a variety of significantly improved functional, structural and economic characteristics. In particular, the compositions of this invention are combination products containing two or more pesticides with a tackifying solvent that dissolves at least one of the pesticides being used to tack at least one other solid pesticide into a unitary, composite, without encountering detrimental chemical interactions between the two or more pesticides. By dissolving one pesticide in the tacking solvent, a range of pesticide concentrations can be generated to then optimize tacking of a granular pesticide or pesticides, preferably in small grain or powdered form, to substrates such as inert carriers, fertilizers and the like. In this way the active ingredient concentrations of the final products can be controlled for all pesticides.

In a preferred embodiment of this invention, bifenthrin technical was found to dissolve in a non-polar polybutene tacking solvent. The bifenthrin active ingredient solution was then used to tack technical atrazine powder onto fertilizer substrate or base. However, in accordance with the present invention, it should be recognized that numerous other composite, combination products can be prepared employing a wide variety of active ingredients.

The following examples are specific illustrations of the practice of the invention in accordance with the foregoing process. All parts and percentages are by weight unless otherwise indicated.

EXAMPLE 1

Bifenthrin technical grade was melted (57-64° C.) in an oven over night and then stirred into a beaker containing polyvis polybutylene L-14 solvent and heated to approximately 50-55 C. The amounts of ingredients were adjusted to form a 13% solution of bifenthrin technical and polybutylene L-14 containing 63.29 grams of bifenthrin technical with a total solution weight of 463.29 grams at 13% bifenthrin concentration. The solution having a brown color was stirred until homogenous at which time it was decanted into 4 four ounce jars and allowed to set at ambient temperatures to produce a tackifying solution for spray coating on the outer surface of selected substrate materials followed by subsequent dusting of the tacky outer surface with a powdered atrazine herbicidally active ingredient which adhered to the tacky surface forming a unitary composite granular composition having an insecticidally active bifenthrin coating in combination with a herbicidally active atrazine layer.

Upon observation over an extended time period of greater than about 21 months, it was observed that the atrazine layer continued to adhere to the coated granular substrate demonstrating the stability of the resulting coated composite granular and, also, the prevention of degradation of the active ingredients included in the granular composition.

EXAMPLE 2

9.8 pounds of methylene urea based granular material were placed in a floor mixer and 51 grams of atrazine was mixed in. 31.75 grams of polybutene L-14 was heated to a temperature of approximately 50-55° C. and 5.22 grams of bifenthrin technical grade which had been melted at about 80° C. was dissolved in the heated polybutene. The resulting bifenthrin solution was sprayed on the granular material and the spray coated composition was allowed to mix for a period of 5-6 minutes to form a granular composite composition which was dry and free flowing in appearance with no dusting problems and which withstood stability and degradation testing.

These finished composite granules then were tested in an accelerated storage stability study conducted in accordance with the Collaborative International Pesticides Analytical Counsel LTD ("CIPAC") procedure for Accelerated Storage (MT 46.3) as provided in CIPAC Handbook Volume J, dated 2000, to determine their chemical and physical stability. The objective of this testing was to simulate the normal long-term ageing of a granular formulation by heating. The accelerated storage study provides an indication of the performance after storage over an extended period of time (up to at least about 2 years) that can be expected of the tested products.

Specifically, a 1 lb sample of the final formulation produced herein was riffled into 17 representative samples for storage and one of these 17 samples was selected for initial analysis without ageing. The remaining 16 storage samples were introduced into separate 4 oz. glass jars, which were subsequently sealed and placed in an oven at a specified temperature (as indicated in Table I below) for a defined period of time (as also indicated in Table I below). These samples were then evaluated at predetermined time intervals at room temperature, 35° C. and 50° C.

As noted above, the time/temperature protocol employed in this testing was in accordance with the CIPAC procedure for Accelerated Storage (MT 46.3). CIPACS's test regimen dictates that 50° C. for 4 weeks and 35° C. for 12 weeks is equivalent to 2 years stability.

TABLE I

Accelerated Stability Study of Atrazine/Bifenthrin Composite Granule on a Methylene Urea Carrier

| Storage Time Period | Temperature Conditions | Percent Atrazine | Percent Bifenthrin |
|---|---|---|---|
| Initial (No Ageing) | Room Temp. | 1.07 | 0.099 |
| 1 Month Ageing | Room Temp. | 1.10 | 0.104 |
| " | 35° C. | 1.05 | 0.103 |
| " | 50° C. | 1.09 | 0.103 |
| 2 Months Ageing | Room Temp. | 1.07 | 0.103 |
| " | 35° C. | 1.03 | 0.103 |
| " | 50° C. | 1.03 | 0.100 |
| 3 Months Ageing | Room Temp. | 0.99 | 0.096 |
| " | 35° C. | 0.99 | 0.100 |
| " | 50° C. | 1.04 | 0.098 |
| 4 Months Ageing | Room Temp. | 0.98 | 0.103 |
| " | 35° C. | 1.06 | 0.106 |
| " | 50° C. | 1.01 | 0.107 |
| 6 Months Ageing | Room Temp. | 1.08 | 0.096 |
| 12 Months Ageing | Room Temp. | 1.05 | 0.109 |
| 18 Months Ageing | Room Temp. | 0.96 | 0.103 |
| 21 Months Ageing | Room Temp. | 1.04 | 0.105 |

From the above tabulated results as well as from visual inspection of the sample products over the test periods, it was determined that the tested products all exhibited excellent physical and chemical stability without degradation of the active ingredients throughout the test period.

EXAMPLE 3

9.80 pounds of blended granular materials including sulfur coated urea, granular urea, DAP, granular KCl, limestone #6 and corn cobs were placed in a floor mixer and 51 grams of atrazine were mixed in. 40.80 grams of polybutene L-14 was heated to a temperature of approximately 50-55 C and 5.22 grams of bifenthrin technical grade which had been melted at about 80 C was dissolved in the heated polybutene. The resulting bifenthrin solution was sprayed on the blend of granular materials and the spray coated composition was allowed to mix for a period of 5-6 minutes to form a granular composite composition which was dry and free flowing in appearance with no dusting problems and which withstood stability and degradation testing performed in accordance with accelerated storage stability study test procedures described above in Example 2. The testing conditions are tabulated below in Table II:

TABLE II

Accelerated Stability Study of Atrazine/Bifenthrin Composite Granule on a Physical Blend of Granular Carriers

| Storage Time Period | Temperature Conditions | Percent Atrazine | Percent Bifenthrin |
|---|---|---|---|
| Initial (No Ageing) | Room Temp. | 106 | 0.107 |
| 1 Month Ageing | Room Temp. | 1.01 | 0.101 |
| " | 35° C. | 1.04 | 0.105 |
| " | 50° C. | 1.05 | 0.103 |
| 2 Months Ageing | Room Temp. | 1.09 | 0.101 |
| " | 35° C. | 1.09 | 0.100 |
| " | 50° C. | 1.05 | 0.099 |
| 3 Months Ageing | Room Temp. | 1.03 | 0.099 |
| " | 35° C. | 1.02 | 0.101 |
| " | 50° C. | 1.00 | 0.099 |
| 4 Months Ageing | Room Temp. | 1.09 | 0.108 |

TABLE II-continued

Accelerated Stability Study of Atrazine/Bifenthrin Composite Granule on a Physical Blend of Granular Carriers

| Storage Time Period | Temperature Conditions | Percent Atrazine | Percent Bifenthrin |
|---|---|---|---|
| " | 35° C. | 1.07 | 0.104 |
| " | 50° C. | 1.02 | 0.104 |
| 6 Months Ageing | Room Temp. | 1.08 | 0.104 |
| 12 Months Ageing | Room Temp. | 1.02 | 0.100 |
| 18 Months Ageing | Room Temp. | 0.95 | 0.995 |
| 21 Months Ageing | Room Temp. | 1.06 | 0.106 |

EXAMPLE 4

Samples of solutions containing non-cyano containing pyrethroid insecticidally active ingredients (bifenthrin and permethrin pesticides) were prepared by dissolving the pyrethroids in a variety of non-polar solvents such as polybutenenes (e.g., L14, L50, H7 and H8), canola oil such as Stepsol ROW-W sold by Stepan Chemical and safflower oil including generic products to demonstrate the solubility and temperature responsiveness of the pyrethroids in such solvents.

Specifically, samples were prepared in 4 ounce glass bottles by combining the non-cyano containing pyrethroids Bifenthrin Technical (supplied by FMC Corporation) and Permethrin Technical sold by Gharda USA, Inc with various non-polar solvents at 10%, 25% and 50% rates by mass (total mass of each sample being 40 grams) so that the 10% formulation contained 4 g of the pyrethroid and 36 g solvent; the 25% formulation contained 10 g of the pyrethroid and 30 g solvent; and the 50% formulation contained 20 g of the pyrethroid and 20 g solvent. Each of the resulting solutions was stirred vigorously in the bottles until a clear solution was obtained. The initial temperatures of the solutions in each of bottles was recorded before the bottles were heated on a laboratory hot plate Each of the solutions was stirred constantly while the solution was being heated on the hot plate and the solutions were frequently observed for signs of any visible separation between the solvent and the solute. There was no evidence of separation of components in any of the bottles demonstrating that the pyrethroid components had all dissolved in the tested non-polar solvents. The final temperature of the solutions in each of the bottles was recorded and it was noted that the temperature required to achieve full miscibility of the pyrethroids in the solvents was up to about 80° C.

In the following Table III, each of the non-cyano containing pyrethroids that were tested and each of the non-polar solvents which were employed with such pyrethroids are listed as well as the initial temperature of the solution and the final temperature resulting in full miscibility of the components.

TABLE III

SOLUBILITY OF NON-CYANO CONTAINING PYRETHROIDS IN SOLVENTS

| Non-Cyano Containing Pyrethroid | Solvent | Percent Pyrethroid | Initial Temp. (° C.) | Final Temp. (° C.) |
|---|---|---|---|---|
| Permethrin Tech. | Polybutene L-14 | 10% | 26 | 26 |
| " | " | 25% | 27 | 28 |
| " | " | 50% | 28 | 31 |

TABLE III-continued

SOLUBILITY OF NON-CYANO CONTAINING PYRETHROIDS IN SOLVENTS

| Non-Cyano Containing Pyrethroid | Solvent | Percent Pyrethroid | Initial Temp. (° C.) | Final Temp. (° C.) |
|---|---|---|---|---|
| Bifenthrin Tech. | " | 10% | 26 | 30 |
| " | " | 25% | 30 | 40 |
| " | " | 50% | 28 | 43 |
| Permethrin Tech. | Polybutene L-50 | 10% | 26 | 35 |
| " | " | 25% | 26 | 51 |
| " | " | 50% | 25 | 54 |
| Bifenthrin Tech. | " | 10% | 25 | 37 |
| " | " | 25% | 28 | 35 |
| " | " | 50% | 30 | 43 |
| Permethrin Tech. | Polybutene H-7 | 10% | 26 | 29 |
| " | " | 25% | 26 | 33 |
| " | " | 50% | 27 | 50 |
| Bifenthrin Tech. | " | 10% | 25 | 45 |
| " | " | 25% | 27 | 41 |
| " | " | 50% | 27 | 41 |
| Permethrin Tech. | Polybutene H-8 | 10% | 25 | 51 |
| " | " | 25% | 26 | 54 |
| " | " | 50% | 26 | 62 |
| Bifenthrin Tech. | " | 10% | 27 | 37 |
| " | " | 25% | 37 | 50 |
| " | " | 50% | 36 | 36 |
| Permethrin Tech. | Canola Oil (Stepsol ROW-W) | 10% | 26 | 26 |
| " | Canola Oil (Stepsol ROW-W) | 25% | 26 | 27 |
| " | Canola Oil (Stepsol ROW-W) | 50% | 26 | 30 |
| Bifenthrin Tech. | Canola Oil (Stepsol ROW-W) | 10% | 26 | 45 |
| " | Canola Oil (Stepsol ROW-W) | 25% | 29 | 57 |
| " | Canola Oil (Stepsol ROW-W) | 50% | 31 | 74 |
| Permethrin Tech. | Safflower Oil | 10% | 32 | 80 |
| " | " | 25% | 30 | 80 |
| " | " | 50% | 32 | 80 |
| Bifenthrin Tech. | " | 10% | 27 | 80 |
| " | " | 25% | 28 | 80 |
| " | " | 50% | 31 | 80 |

EXAMPLE 5

This example illustrates the preparation of a granular composite composition comprising a corn cob granular substrate material coated with a tackifying solution formed from a non-cyano containing pyrethroid (Permethrin Technical) dissolved in a non-polar solvent (canola oil) and having a powdered pesticidally active ingredient (Prodiamine herbicide) applied on the coated outer surface of the granular substrate.

In preparation, 248.82 g of canola oil (Stepsol ROW-W) is added to a beaker and is heated to 60° C. while agitating. After the canola oil reaches temperature in the beaker, 27.75 g of Permethrin Technical, which has been liquefied by preheating to a temperature of approximately 60° C. in an oven, is added to the heated canola oil solvent with agitation. The temperature of the mixture is maintained at about 60° C. until a clear solution containing 10% by weight Permethrin (276.57 g) is formed.

Then, 10.71 lbs of 14/40 corn cobs are charged in a Munson blender and while the blender is running, 80.23 g of powdered Prodiamine 65 MC herbicide supplied by Makhteshim-Agan of North America, Inc. comprising 65% Prodiamine-2,4-dinitro-N3-dipropyl-6-(trifluoromethyl)-1,3-benzenediamine) is added in the mixer and is allowed it to blend with the corn cobs. After about 10 seconds, all of the above described 10% Permethrin solution is sprayed onto the blending composite materials and blending is continued until the resulting product is uniform with the 10% Permethrin solution causing the blending materials to become tacky allowing the Prodiamine powder to adhere to the surface of the corn cob substrate resulting in a uniform composite granular composition of corn cobs with the two pesticidally active ingredients (Permethrin and Prodiamine).

Although the invention has been described in its preferred forms with a certain degree of particularity, it is to be understood that the present disclosure has been made by way of example only. Numerous changes in the details of the compositions and in the operational steps of the methods and in the compositions utilized therein will be apparent without departing from the spirit and scope of the invention, as defined in the appended claims.

We claim:
1. A composition comprising:
    a granular substrate,
    a coating layer over the granular substrate, the coating layer comprising a blend of
    a) a non-cyano containing pyrethroid insecticidally active ingredient,
    b) a non-polar tackifier, and
    c) a small grain or powdered pesticidally active ingredient, wherein the small grain or powdered pesticidally active ingredient is an herbicidally active ingredient,
    wherein polar solvent is absent from the coating layer,
    and wherein the small grain or powdered herbicidally active ingredient comprises atrazine or metsulfuron methyl, or mixtures thereof.
2. The composition of claim 1 wherein the herbicidally active ingredient comprises atrazine.
3. The composition of claim 1 wherein the pyrethroid insecticidally active ingredient comprises allethrin, barthrin, bifenthrin, bioallethrin, bioresmethrin, biopermethrin, dimethrin, esbiol, furethrin, permethrin, resmethrin, tetramethrin, or mixtures thereof.
4. The composition of claim 1 wherein the pyrethroid insecticidally active ingredient has the structural formula:

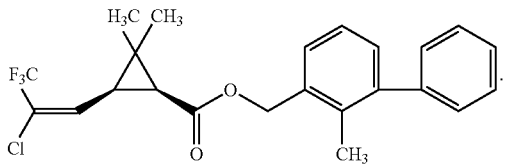 [SMILES: Cc1c(COC(=O)[C@H]2[C@@H](/C=C(/Cl)C(F)(F)F)C2(C)C)cccc1-c1ccccc1]

5. The composition of claim 1 wherein the granular substrate comprises fertilizer granules, inert carriers, or mixtures thereof.
6. The composition of claim 1 wherein the granular substrate comprises an inert carrier.
7. The composition of claim 6 wherein the inert carrier comprises corn cobs, peanut hulls, coffee bean husks, pelletized limestone, dolomite, biological granules or mixtures thereof.
8. The composition of claim 1 wherein the granular substrate comprises a fertilizer granule.
9. The composition of claim 1 wherein the tackifier comprises cottonseed oil, linseed oil, soybean oil, canola oil, coconut oil, corn oil, fish oil, hydrogenated vegetable oils, fatty acid esters, olive oil, palm oil, paraffin wax, peanut oil, safflower oil, mineral oil, greater than 10 carbon alkenes, polymerized alpha olefins, oxidized plant oils, oil polymerizates, methyl oleate, pine oil, petrolatum, PPG mono oleate, rape oil methyl ester, or mixtures thereof.

10. The composition of claim 1 wherein the tackifier is of the formula:

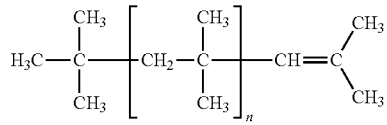

wherein n ranges from about 2 to about 20.

11. The composition of claim 10 wherein n ranges from about 4 to about 6.

12. The composition of claim 10 wherein the tackifier is polybutene having a molecular weight of about 370.

13. The composition of claim 12 wherein n=4.59.

14. The composition of claim 10 wherein the tackifier is polybutene having a molecular weight of about 430.

15. The composition of claim 14 wherein n=5.66.

16. The composition of claim 10 wherein the tackifier is polybutene having a molecular weight of about 440.

17. The composition of claim 16 wherein n=5.84.

18. The composition of claim 10 wherein the tackifier is polybutene having a molecular weight of about 490.

19. The composition of claim 18 wherein n=6.73.

20. The composition of claim 1 wherein the pesticidally active ingredient is atrazine and the insecticidally active ingredient is bifenthren.

21. The composition of claim 1 wherein the pesticidally active ingredient is atrazine, the insecticidally active ingredient is bifenthren, and the tackifier is polybutene.

22. A composition comprising:
i. a granular substrate;
ii. a coating layer over the granular substrate, the coating layer comprising a blend of
   a) a non-cyano containing pyrethroid insecticidally active ingredient, and
   b) a non-polar tackifier,
   wherein polar solvent is absent from the coating layer; and
iii. a small grain or powdered pesticidally active ingredient adhered on the coating layer, wherein the small grain or powdered pesticidally active ingredient is atrazine or metsulfuron methyl, or mixtures thereof.

23. The composition of claim 22 wherein the pyrethroid insecticidally active ingredient has the structural formula:

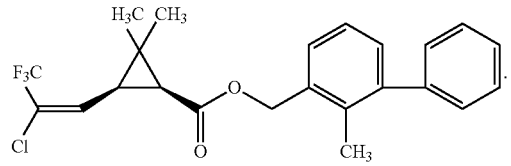 [SMILES: Cc1c(COC(=O)[C@H]2[C@@H](/C=C(/Cl)C(F)(F)F)C2(C)C)cccc1-c1ccccc1]

24. The composition of claim 22 wherein the tackifier is of the formula:

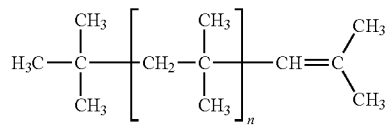

wherein n ranges from about 2 to about 20.

25. The composition of claim 24 wherein n ranges from about 4 to about 6.

26. The composition of claim 22 wherein the pesticidally active ingredient is atrazine and the insecticidally active ingredient is bifenthren.

27. The composition of claim 22 wherein the pesticidally active ingredient is atrazine, the insecticidally active ingredient is bifenthren, and the tackifier is polybutene.

28. The composition of claim 1, wherein the herbicidally active ingredient is metsulfuron methyl.

29. The composition of claim 1, wherein the herbicidally active ingredient is metsulfuron methyl and the insecticidally active ingredient is bifenthren.

30. The composition of claim 22, wherein the pesticidally active ingredient is atrazine.

31. The composition of claim 22, wherein the pesticidally active ingredient is metsulfuron methyl.

* * * * *